(12) United States Patent
Zhu et al.

(10) Patent No.: US 7,112,448 B2
(45) Date of Patent: Sep. 26, 2006

(54) MBTH FOR ALIPHATIC ALDEHYDE MEASUREMENT

(75) Inventors: Peter Zhu, Irvine, CA (US); Szu-Min Lin, Laguna Hills, CA (US)

(73) Assignee: Ethicon, Inc., Somerville, NJ (US)

( * ) Notice: Subject to any disclaimer, the term of this patent is extended or adjusted under 35 U.S.C. 154(b) by 270 days.

(21) Appl. No.: 09/810,889

(22) Filed: Mar. 16, 2001

(65) Prior Publication Data

US 2002/0168777 A1  Nov. 14, 2002

(51) Int. Cl.
*G01N 33/00* (2006.01)
(52) U.S. Cl. .................................. 436/128; 436/127
(58) Field of Classification Search ................ 436/127, 436/128, 130, 164, 177; 422/58, 68.1
See application file for complete search history.

(56) References Cited

U.S. PATENT DOCUMENTS

| 3,645,696 A | * | 2/1972 | Iannacone et al. | .......... 436/166 |
| 4,436,754 A | * | 3/1984 | Jacobs | .......... 514/694 |
| 4,471,055 A | | 9/1984 | Opp | .......... 436/128 |
| 4,703,763 A | * | 11/1987 | McAlister | .......... 600/578 |

FOREIGN PATENT DOCUMENTS

| EP | 0016578 A1 | 1/1980 |
| EP | 0016578 B1 | 1/1980 |
| EP | 0 769 58 A1 | 4/1997 |
| FR | 2 198 642 A | 3/1974 |

OTHER PUBLICATIONS

Analytical Chemistry, *The 3-Methyl-2-benzothiazolone Hydrazone Test*, vol. 33, No. 1, Jan. 1961, pp. 93-96, Eugene Sawicki, Thomas R. Hauser, Thomas W. Stanley, and Walter Elbert.
Analytical Chemistry, *Increasing Sensitivity of 3-Methyl-2-Benzothiazolone Hydrazone Test for Analysis of Aliphatic Aldehydes in Air*, vol. 36, No. 3, Mar. 1964, pp. 679-681, Thomas R.Hauser and Rodney L. Cummins.
Health Lab. Sci. *Tentative Method of Analysis for Formaldehyde Content of The Atmosphere (MBTH-Colorimetric Method-Applications To Other Aldehydes)*, vol. 7, No. 3, Jul. 1970, pp. 173-178, Smith, et al.
Marine Chemistry, *A Colorimetric Procedure for the Determination of Aldehydes in Seawater and in Cultures of Methylotrophic Bacteria*, 17 (1985) 199-212, Elsevier Science Publishers B.V., Amsterdam; Maja A. Eberhardt and John McN. Sieburth.
Correspondence (Feb. 28, 2001) and copies of advertising from Kem Medical Products Corp. Farmingdale NY re its products for glutaraldehyde and OPA neutralizing and disposal.
Material Safety Data Sheet for KemSure™ Neutralizer for OPA disinfectant solution (Sep. 1, 2000).
Material Safety Data Sheet for GLUT-RX™ Neutralizer for glutaraldehyde disinfectant solution (Dec. 1, 2000).

* cited by examiner

*Primary Examiner*—Jill Warden
*Assistant Examiner*—LaToya C. Younger

(57) ABSTRACT

A new method is proposed where a limited amount of MBTH is used to detect a point of interest (POI) of an aldehyde in a test sample. Preferably, it reacts with aldehyde first to form an azine. Only if there is remaining MBTH, it is oxidized to another species which combines with the azine to form formazan. However, if there is enough aldehyde, all the MBTH is converted to azine and there is no formation of blue color. Thus, by using the limiting agent MBTH to test the amount of aldehyde around the point of interest, then less aldehyde would produce more blue color and more aldehyde would produce less blue color. This method is especially useful in the quality control of aldehyde products. The end color may be different depending upon the order of addition of the reactants. For example, if an oxidizing agent and MBTH are mixed before adding the aldehyde, a light green to green/blue color results. This method could be used for solution test or for tests on a solid phase such as on nylon membrane. The latter also could be used for measurements with a device or instrument such as a color reader and used in combination with a second aldehyde tester and a pH tester.

18 Claims, 8 Drawing Sheets

MBTH FOR ALIPHATIC ALDEHYDE MEASUREMENT

BACKGROUND OF THE INVENTION

1. Field of the Invention

The field of the invention relates to a method to detect a point of interest (POI) of an aldehyde in a test sample such as a disinfectant. In some embodiments, a device or test strip are used to detect the point of interest of the aldehyde in the test sample.

2. Description of the Related Art

MBTH (3-methyl-2-benzothiazolinone hydrazone hydrochloride) is a well-known aldehyde analysis reagent. Using this reagent, an azine is formed between an aldehyde and MBTH. MBTH is also oxidized by an oxidizing agent such as ferric chloride to another species, which combines with the azine to form a blue colored formazan structure. This reaction was originally described by Sawicki et al. (Sawicki et al. (1961) Analytical Chemistry vol. 33 (1): 93–96) as an extremely sensitive assay for detection of aldehydes in exhaust fumes. The method of Sawicki et al. was subsequently modified to achieve even higher sensitivity to allow detection of aldehydes in air in the parts-per-billion range (Hauser et al. (1964) Analytical Chemistry vol. 36 (3): 679–681).

EP 0 016 578 teaches application of the reaction of MBTH with aldehydes to aqueous samples. The assay was useful with samples in the parts per million range. The MBTH procedure was also adapted for use in seawater samples to measure the formaldehyde given off by the marine methanotroph, *Methylomonas pelagica* (Eberhardt et al. (1985) Marine Chemistry vol. 17: 199–212). This method has proven very useful in analysis of dilute aldehyde-containing samples. However, for concentrated aldehyde analysis, this method is inconvenient due to the need for dilutions. A new method is proposed here for use of the MBTH procedure with samples which contain higher concentrations of aldehydes such as disinfectants.

SUMMARY OF THE INVENTION

The present invention pertains to a method of determining the presence of a point of interest of an aldehyde in a test sample comprising the steps of:
1) reacting the aldehyde in the test sample with an amount of MBTH, wherein the amount is sufficient to react with the aldehyde to the point of interest to produce an azine;
2) oxidizing MBTH with an oxidant;
3) reacting the azine and the oxidized MBTH to form a formazan and produce a color change;
4) observing the color in the test sample after the above two reaction and oxidizing steps; and
5) determining the presence of an excess of aldehyde in the test sample to the point of interest by observation of the color of the test sample.

In a preferred embodiment, the color in the test sample is blue, green, yellow or any combination thereof. In a preferred embodiment, the oxidant is selected from the group including ferric chloride, potassium ferricyanide, lead tetraacetate and periodic acid. In a most preferred embodiment, the oxidant is ferric chloride. In a preferred embodiment, the aldehyde is glutaraldehyde.

In a preferred embodiment, the oxidant is mixed with the test sample at the same time as the MBTH reacts with the aldehyde. In an alternate preferred embodiment, the oxidant is added to the test sample after the MBTH reacts with the aldehyde.

In a preferred embodiment, the method further includes drawing up a fixed volume of an aldehyde-containing test sample before or during the reaction of aldehyde with MBTH. In a more preferred embodiment, the method includes loading the fixed volume to a measuring device having a gas or vapor permeable but liquid impermeable membrane. In a more preferred embodiment, the method includes loading the fixed volume to a measuring device containing the MBTH or $FeCl_3$.

In a preferred embodiment, the aldehyde in the test sample is applied to an absorbent material. In a more preferred embodiment, the absorbent material is a nylon membrane. In a most preferred embodiment, the absorbent material contains MBTH or $FeCl_3$.

The present invention also pertains to a liquid measuring device including at least one compartment for determining the presence of a point of interest of an aldehyde in a test sample including a first compartment having a proximal and distal end which contains an amount of MBTH that reacts with a aldehyde in a first reacting step, wherein said amount is sufficient to react with the aldehyde to the point of interest. In a preferred embodiment, the first compartment further includes an oxidant that reacts with the MBTH.

In a preferred embodiment, the liquid measuring device further includes a second compartment in liquid communication with the first compartment by means of a valve. In a more preferred embodiment, the second compartment contains an oxidant that reacts with the MBTH.

In a preferred embodiment, the liquid measuring device is a syringe or pipet.

In a preferred embodiment, the liquid measuring device further includes a gas or vapor permeable but liquid impermeable membrane between the proximal and distal end of the first compartment. In a preferred embodiment, the liquid measuring device may also include a filter at or near the distal end of the first compartment. In a preferred embodiment, the liquid measuring device further includes a valve at or near the distal end of the first compartment. In a preferred embodiment, the liquid measuring device further includes a needle assembly.

In a preferred embodiment, the aldehyde in the test sample is selected from the group consisting of glutaraldehyde and formaldehyde.

The present invention also pertains to a test strip including at least one absorbent material for determining the presence of a point of interest of an aldehyde in a test sample including a first absorbent material which contains an amount of MBTH that reacts with an aldehyde in a first reacting step, wherein the amount is sufficient to react with the aldehyde to the point of interest.

In a preferred embodiment, the first absorbent material of the test strip further includes an oxidant that reacts with the MBTH. In a preferred embodiment, the test strip further includes a second absorbent material containing an oxidant that reacts with the MBTH. In a more preferred embodiment, the second absorbent material is separated from the first absorbent material with a separator. In a most preferred embodiment, the separator includes a removable liquid impermeable film or a blank absorbent material.

In a preferred embodiment, the test strip further includes an aldehyde tester. In a more preferred embodiment, the aldehyde tester is a Shiff's reagent.

In a preferred embodiment, the test strip further includes a pH tester. In a more preferred embodiment, the pH tester includes a pH dye indicator selected from the group including bromothymol blue, brilliant yellow, neutral red, rosolic acid, phenol red, 3-nitrophenol, orange II, phenolphthalein, o-cresolphthalein, nile blue A and thymolphthalein.

In a preferred embodiment, the test strip further includes at least one color comparator.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIGS. 6A and 6B show embodiments of the liquid delivery apparatus with all chemicals in one chamber. FIG. 6C shows a two chambered embodiment of the liquid delivery apparatus. The test sample may be taken into the first chamber for reaction with the first compound such as MBTH in FIG. 1. Then the sample is moved by means of a one-way valve or a manual ON/OFF valve 8 into the second chamber where the test sample reacts with the second compound such as $FeCl_3$ of FIG. 1.

FIGS. 9A–E show 5 variations of a tester strip.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Figure 1:
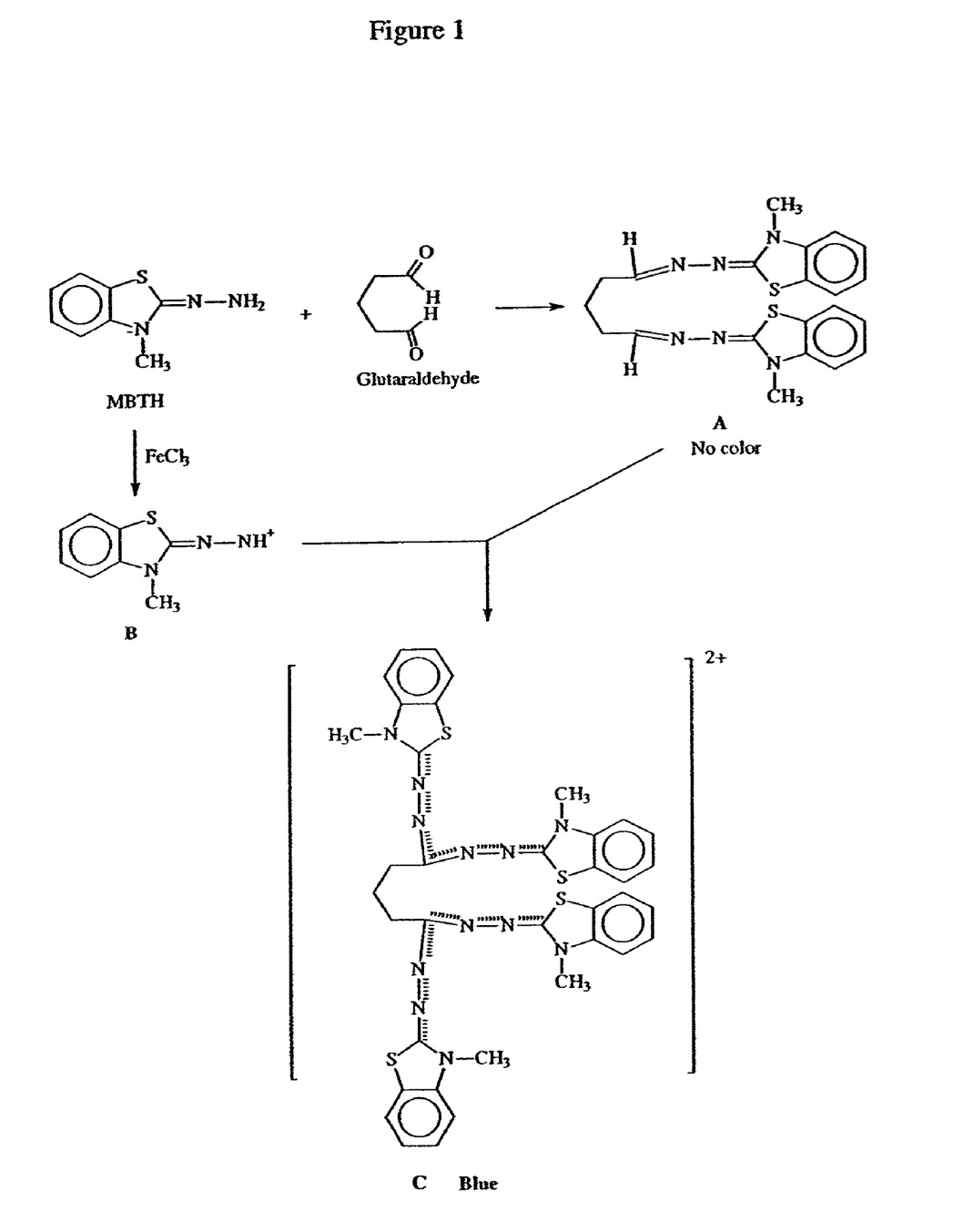
FIG. 1 shows the MBTH-glutaraldehyde color reaction principle. MBTH combines with an aldehyde to form a colorless azine (A) and MBTH is oxidized to a species (B). Intermediate A and B react to form (C), a formazan.

Using MBTH, an azine is formed between an aldehyde and MBTH. Referring to FIG. 1, MBTH is also oxidized by an oxidizing agent such as ferric chloride to another species B, which combines with an azine A to form a blue colored formazan structure C. For concentrated aldehyde analysis, however, this method is inconvenient due to the need for dilutions. A new method is proposed here where a limited amount of MBTH is used.

In the method of the invention, if a limited amount of MBTH is added to a test sample containing an aldehyde, the MBTH reacts with the aldehyde to form an azine A. Only if there is remaining MBTH, will the MBTH be oxidized to another species, B, which combines with the azine A to form formazan C. However, if there is enough aldehyde, all of the MBTH will be converted to an azine A, the oxidant will have nothing to react with so formazan C will not be formed and there will be no blue color. Thus, by using a limited amount of MBTH, if the amount of aldehyde is more than what MBTH can react, then all of the MBTH reacts to form the azine A and no blue color is observed. However, if the aldehyde is less than what MBTH can react, some of the MBTH will be oxidized to another species B which reacts with azine to form formazan C and give a blue color. By the use of a limited amount of the agent MBTH to test the amount of aldehyde around the point of interest (POI), less aldehyde will produce more blue color and more aldehyde will produce less blue color. This is further illustrated below.

While the prior art teaches the aldehyde as the limiting reagent, in the method disclosed herein, MBTH is the limiting reagent. The amount of MBTH is just enough to neutralize the aldehyde at the point of interest. While MBTH is the preferred embodiment, other hydrazones may also be used such as salicylalhydrazone and p-nitrobenzalhydrazone. Likewise, other reagents may be used as the oxidizing agents including ferric chloride, potassium ferricyanide, lead tetraacetate, and periodic acid. In a most preferred embodiment, ferric chloride is used as the oxidizing agent.

The order in which the chemicals are added is important for the final color observed. For example, if MBTH is added first and ferric chloride is added last, then the final color of the solution will be light yellow when the concentration of glutaraldehyde is equal to or above the POI and will be blue when the glutaraldehyde concentration is below the POI. On the other hand, if ferric chloride and MBTH are mixed first, the final color of the solution after adding the aldehyde will vary from light green to green/blue depending upon the amount of aldehyde in the test sample. In this case, a meter or color comparator may be needed to determine the amount of the aldehyde compared to the POI.

Another aspect of the invention is a liquid-measuring device, such as a pipette or syringe, for carrying out the assay. This device could be used for any "fixed-volume" measurement and transfer in chemistry, biochemistry, clinical chemistry or other industries.

The apparatus may be a syringe or pipette with one or more barrels and plungers and a membrane barrier with or without a coupling device. The membrane barrier is a gas or vapor permeable and liquid impermeable barrier. In the presence of certain pressure differences between the two sides of the barrier, the gas or vapor flows through the membrane but not the liquid. Any suitable gas or vapor permeable and liquid impermeable materials can be used for this purpose. Some examples include, but are not limited to, nonwoven polyolefin, such as Tyvek™ (non-woven polyethylene), or CSR (non-woven polypropylene central supply room), wrapping material and any other hydrophobic filtering materials. Optionally, the device contains an insert and a holder. The syringe or pipette apparatus may also contain valves to control the flow of liquid.

The membrane barrier can be thermally bound to the syringe or pipet. It can also be attached to the syringe or pipet with an adhesive or connected to the syringe barrel by a coupling device. The coupling device may be connected to an insert for altering the position of the membrane barrier. The position of the membrane barrier can be adjusted by the length of the insert. The insert may be secured with a holder.

The membrane barrier is a gas or vapor permeable but liquid impermeable barrier. The membrane barrier is positioned such that the liquid can only be filled up to the barrier. The invention has several preferred embodiments.

Figure 2:
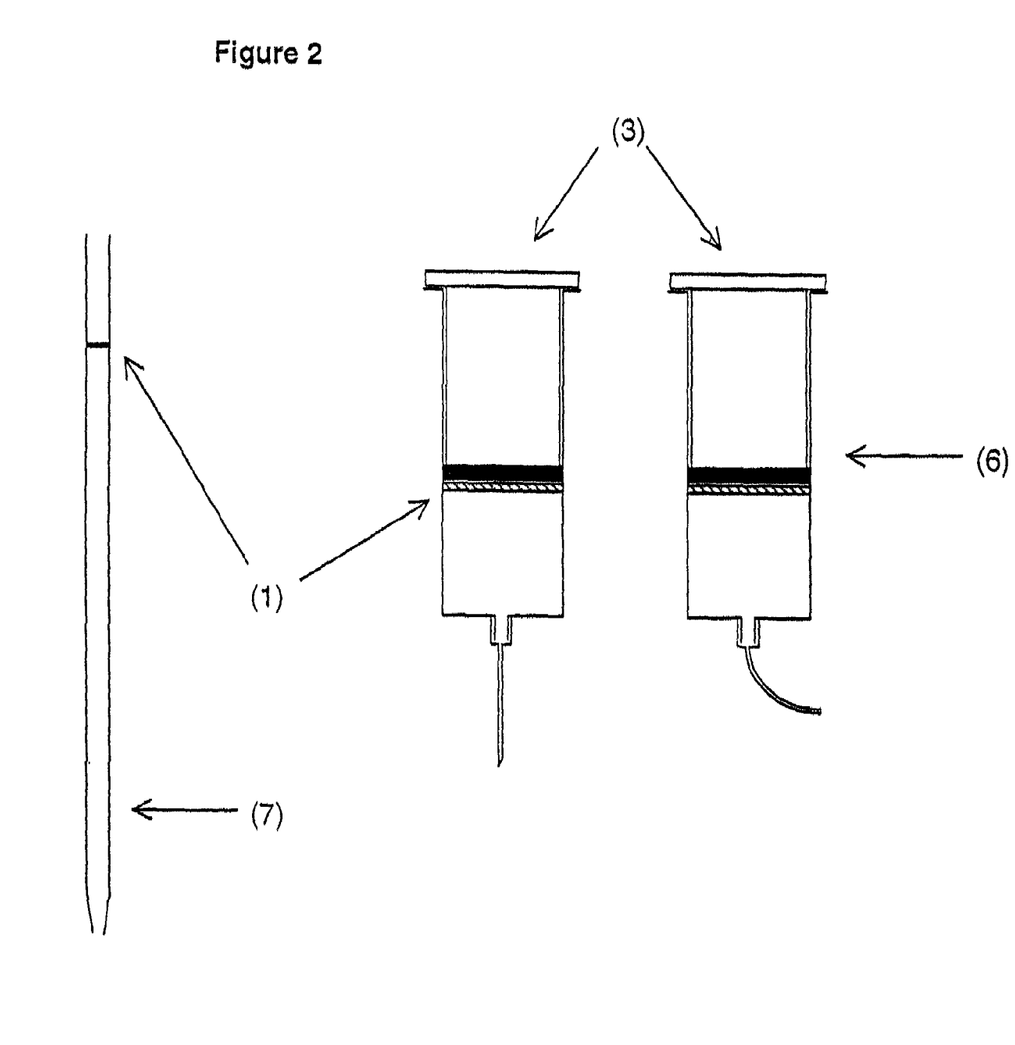
FIG. 2 shows a pipette and two variants of a syringe with a gas or vapor permeable liquid impermeable barrier.

In the first embodiment (FIG. 2), a gas or vapor permeable liquid impermeable membrane 1 is fixed into the pipette 7 or syringe 6 and held in place at the desired maximum volume by means known in the art. The syringe includes a plunger 3. The syringe can have a metal or plastic needle with or without a needle cap. In one embodiment (FIGS. 3A–3D), a coupling device 2 is used which is larger or smaller than the diameter of the pipette 7 or syringe 6. Two parts of the pipet or syringe with different lengths can be joined together with such a coupling device.

Figure 3:
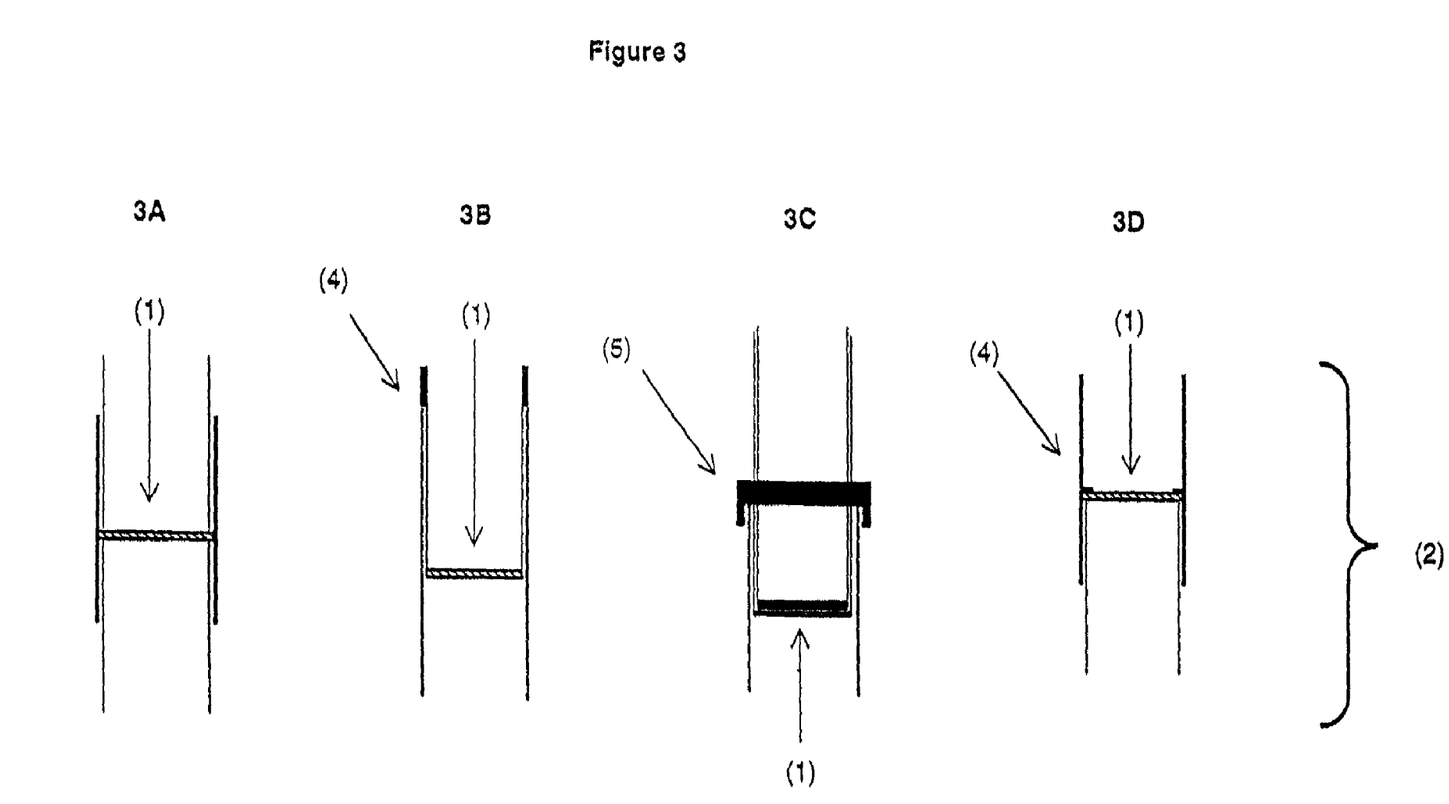
FIG. 3A shows the coupling of the gas or vapor permeable liquid impermeable barrier to the syringe or pipette.
FIG. 3B illustrates how inserts 4 at the top of the pipette or syringe attach the gas or vapor permeable liquid impermeable barrier to the pipette or syringe.
FIG. 3C illustrates a holder 5 that holds the inserts in place.
FIG. 3D shows the inserts and the coupling of the gas or vapor permeable liquid impermeable barrier.
Figure 4:
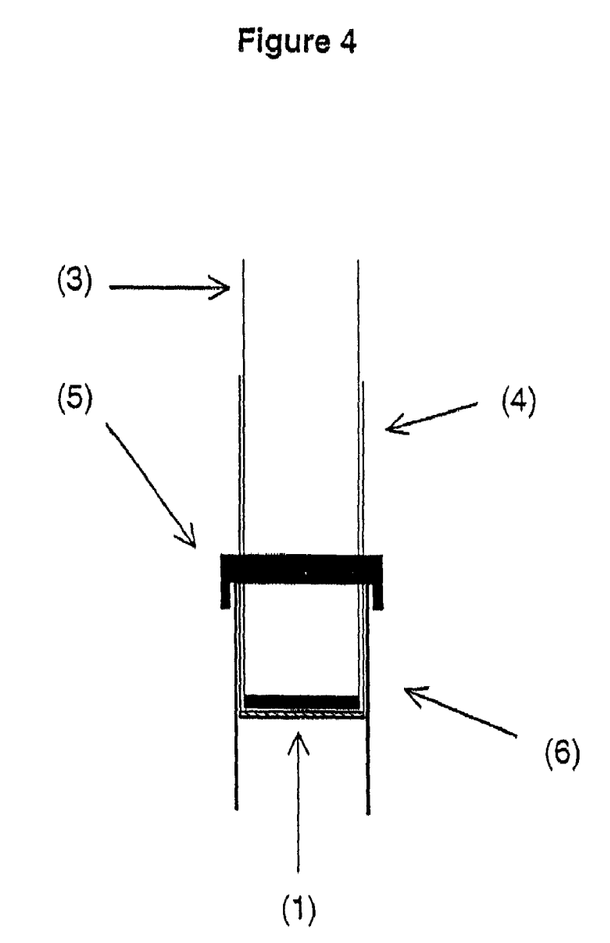
FIG. 4 is an expanded view of FIG. 3C which shows a gas or vapor permeable liquid impermeable barrier 1, an insert 4, and a holder 5.
Figure 5:
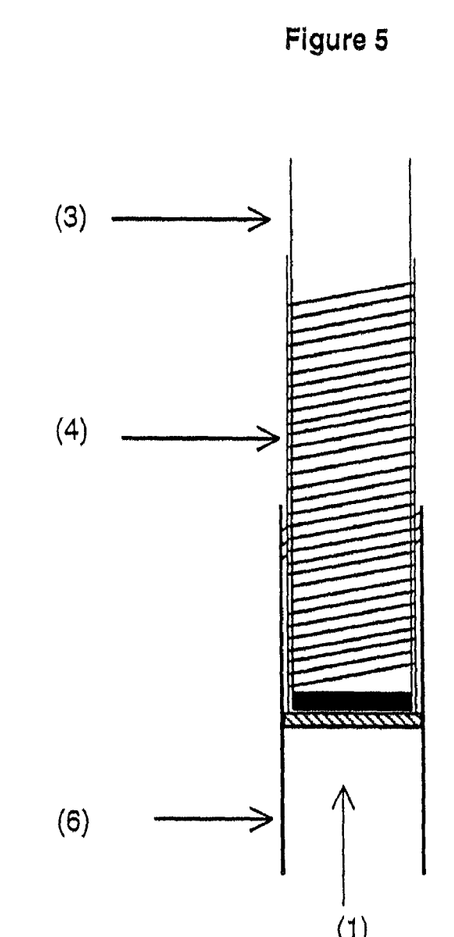
FIG. 5 shows one embodiment of the invention where the position of the gas or vapor permeable liquid impermeable membrane is adjusted by means of a screw.

Coupling of the membrane barrier to the syringe or pipette is shown in FIGS. 3A, 3B, 3C, 3D and FIG. 4. The membrane can be inserted into the syringe or pipet from the top of the pipette or syringe by an insert 4 which may be secured with a holder 5 and its position varied by any means known in the art such as by a screw (FIG. 5) or a slidable adjustment (FIG. 4). FIG. 3D shows an insert which has a larger diameter than the pipette or syringe. By adjusting the insert and creating a negative pressure on the upper part of the pipette or syringe, the fluid can be loaded into the syringe or pipette up to the barrier.

Figures 6, 6B:
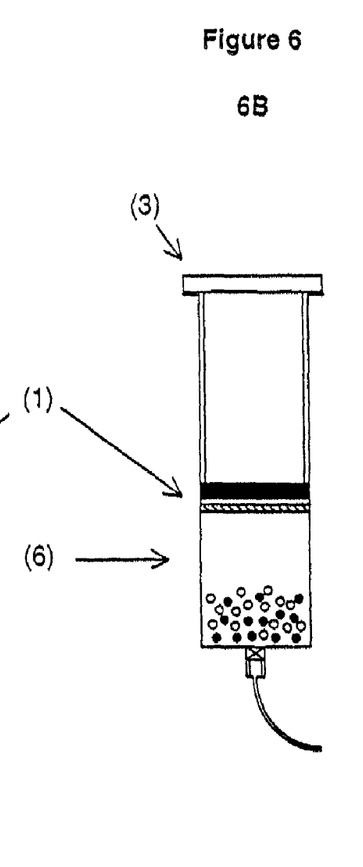
Figure 7:
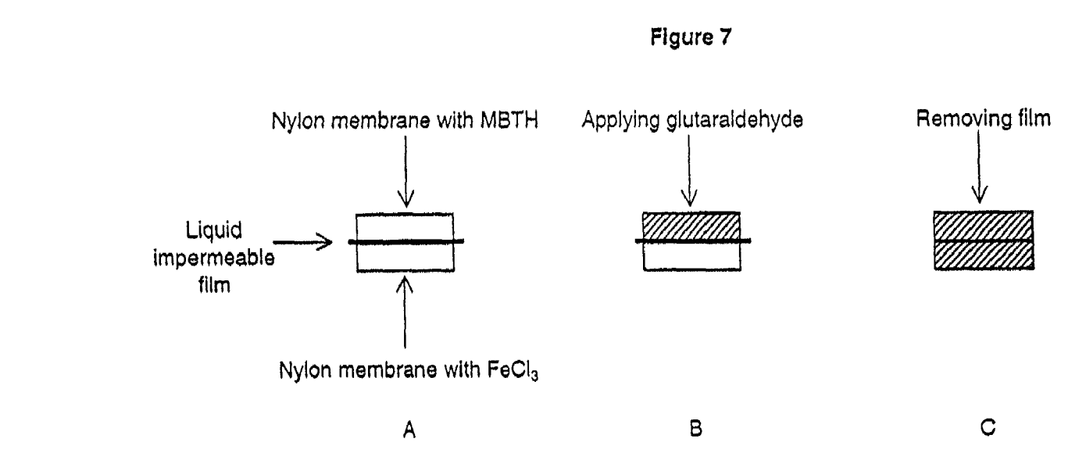
FIG. 7A shows a two-layered nylon membrane where the bottom layer comprises $FeCl_3$, the top layer comprises MBTH and the two layers are separated by a liquid impermeable film.
FIGS. 7B and 7C show the nylon membrane after application of glutaraldehyde at an earlier stage (FIG. 7B) and a later stage (FIG. 7C).

FIGS. 6A, 6B and 6C illustrate the use of the measuring device with this invention. FIGS. 6A and 6B show a syringe with a gas or vapor permeable liquid impermeable barrier and two chemicals. The liquid can be filled in the syringe by inserting the plastic needle into the sample solution, pulling the plunger to create a negative pressure in the syringe, and loading the liquid into the syringe. The measuring device can have a filtering material (FIG. 6A) or valve (FIG. 6B) to retain the chemicals in the barrel. The chemical in the syringe can be in either a liquid or solid form. The valve can be a one-way valve or a manual ON/OFF valve.

FIG. 6C provides another embodiment for mixing more than one reactant successively. It has two chambers 9, 10. A fixed volume of any solution including, but not limited to an aldehyde is drawn up through a one-way valve or an ON/OFF valve 8 into the first chamber 9 where it mixes with the first reactant, for example MBTH. After a predetermined time, the reactants flow through a second one-way valve or an ON/OFF valve 8 into a second reaction chamber 10 which might contain an oxidant such as $FeCl_3$, for example, to complete the reaction. Alternatively, a three-way valve can be used instead of two one-way valves.

EXAMPLES

Example 1

General Color Observation with Excess of MBTH.

In a 2 mL vial containing about 1 mg MBTH, 0.5 mL water was added to form a colorless solution. About 0.2 mL Cidex glutaraldehyde solution (un-activated, 2.4%) was added and the solution became milky (formation of A). About 0.2 mL 1.0% ferric chloride ($FeCl_3$) was added. A blue color formed in about 1 minute (formation of C).

Example 2

General Color Observation without $FeCl_3$.

Example 1 was repeated. However, no $FeCl_3$ was added. The solution remained milky with no blue color.

Example 3

General Color Observation without Glutaraldehyde.

Example 1 was repeated. However, no glutaraldehyde was added. The solution appeared light yellow after the addition of $FeCl_3$ ($FeCl_3$ color).

Example 4

The Effect of the Order of Reagent Addition on Color with Excess of MBTH.

In a 2 mL vial containing about 1 mg MBTH, 0.5 mL water was added to form a colorless solution. About 0.2 mL 1.0% ferric chloride ($FeCl_3$) was added. The solution became light yellow. About 0.2 mL Cidex glutaraldehyde solution (un-activated, 2.4%) was added and the solution turned from light yellow to green in 2 minutes and the green color darkened in 5 minutes.

Thus, a different addition order resulted in a different final color. Green/Blue color instead of blue color formed in this case due to the addition of MBTH first, $FeCl_3$ second and aldehyde last.

Example 5

Color Observations with Different Amounts of Glutaraldehyde.

The procedure in Example 1 was repeated except different amounts of aldehyde were added (see Table 1). The MBTH (0.1% in water) was added first, Cidex (1.75%) was added second and $FeCl_3$ (2.5%) was added third.

TABLE 1

Comparison of Different Amount of Glutaraldehyde.

| Exp # | MBTH (1st add) | Cidex (1.75%) | $FeCl_3$ (2.5%) | Observation |
|---|---|---|---|---|
| 1 | 1000 μL | 60 μL, no wait | 100 μL, fresh | All samples turned blue quickly (<10"). |
| 2 | 1000 μL | 40 μL, no wait | 100 μL, fresh | |
| 3 | 1000 μL | 20 μL, no wait | 100 μL, fresh | Blue color darkness of 3 > 2 > 1 was observed. |

As can be seen, a blue color developed quickly in all samples in less than 10 seconds. However, the intensity of the blue color was 3>2>1. This was not expected. Why did less aldehyde produce a darker blue color?

This could be explained by examining FIG. 1. Since MBTH is not always sufficient, it reacts with aldehyde first to form an azine. Only if there is remaining MBTH, it is oxidized to another species which combines with the azine to form formazan. However, if there is enough aldehyde, all the MBTH is converted to azine and an oxidant could not get anything to react with so formazan was not formed (no blue color). Thus, by using the limiting agent MBTH to test the amount of aldehyde around the point of interest, less aldehyde would produce more blue color and more aldehyde would give less blue! This method is especially useful in the quality control of aldehyde products where a quick assay can be conducted without tedious dilutions.

Also note the wide range of aldehyde used in Table 1. In Exp. #3, about 33% of the amount of aldehyde of Exp. #1 was used. This range is sufficient to develop a practical assay.

Example 6

General Color Observation Using Different Amounts of Glutaraldehyde

As shown in Table 2, to a 2 mL vial, varying amounts of Cidex glutaraldehyde were added first, MBTH was added second and the oxidant $FeCl_3$ was added last.

TABLE 2

General Color Observation, Different Amount of Glutaraldehyde.

| Exp # | Cidex Glutaraldehyde | MBTH | $FeCl_3$ | Observation |
|---|---|---|---|---|
| 1 | 2.1% 100 μL | 0.1%, 500 μL | 2.5%, 100 μL | Yellow |
| 2 | 1.75% 100 μL | 0.1%, 500 μL | 2.5%, 100 μL | 2, 3, 4 are all turned blue quickly. Blue color darkness 4 > 3 > 2 was observed. |
| 3 | 1.50% 100 μL | 0.1%, 500 μL | 2.5%, 100 μL | |
| 4 | 1.40% 100 μL | 0.1%, 500 μL | 2.5%, 100 μL | |

Thus, by using a limited amount of MBTH, if the amount of aldehyde is more than what MBTH can react, then all of the MBTH reacts to form the azine A and no blue color is observed. However, if the aldehyde is less than what MBTH can react, some of the MBTH will be oxidized to another species B which reacts with azine to form formazan C and give a blue color. Although in each of Experiments 2, 3, and 4 above the final color was blue, a clear difference was observed that could be differentiated spectroscopically. By the use of a limited amount of the agent MBTH to test the amount of aldehyde around the point of interest, less aldehyde will produce more blue color and more aldehyde will produce less blue color.

Example 7

General Color Observation on Nylon Membrane with an Excess of MBTH.

A solution containing 1% MBTH and 1% $FeCl_3$ was prepared fresh using MeOH as the solvent. Nylon membranes are soaked in this solution briefly and air-dried. Cidex glutaraldehyde was dropped on the nylon membrane containing both MBTH and $FeCl_3$ (Table 3). Alternatively, other absorbent hydrophilic or porous materials can be used.

TABLE 3

Color Reaction of Glutaraldehyde on nylon membrane with MBTH and $FeCl_3$ located on the same membrane.

| Cidex Glutaraldehyde | Observation |
|---|---|
| Color Green/blue | Color develops in less than 1 min and stabilizes for more than 10 minutes. |

Thus the assay may be easily carried out on a nylon membrane.

Example 8

General Color Observation on Nylon Membrane with an Excess of MBTH and with MBTH and $FeCl_3$ Located on Two Separate Membranes.

Figure 8:
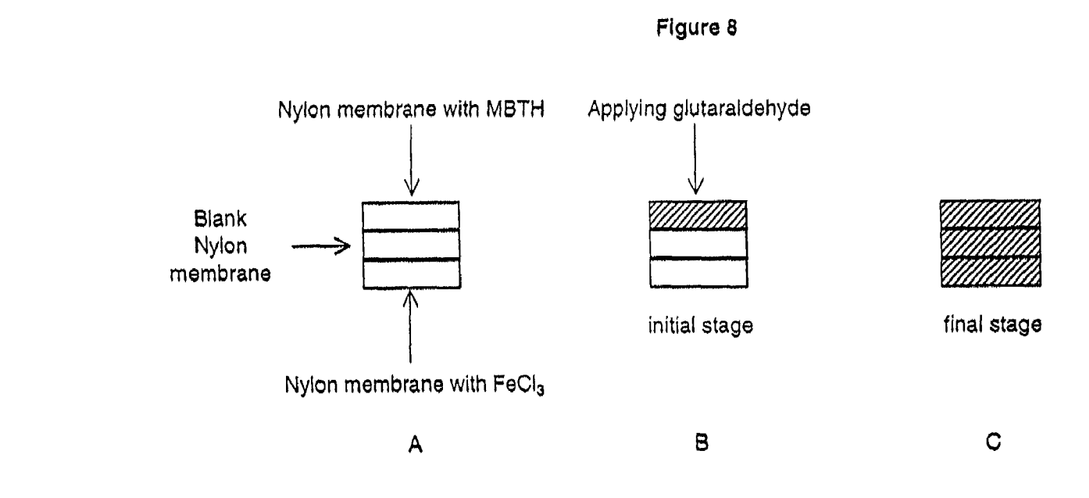
FIG. 8A shows a three layered nylon membrane where the bottom layer comprises $FeCl_3$, the top layer comprises MBTH and the two layers are separated by a blank nylon membrane.
FIGS. 8B and 8C show the nylon membrane after application of glutaraldehyde at an earlier stage (FIG. 8B) and a later stage (FIG. 8C).

Two solutions containing 1% MBTH and 1% $FeCl_3$ were prepared separately fresh using MeOH as the solvent. Nylon membranes were soaked in solutions briefly and air-dried (FIG. 8A). Cidex glutaraldehyde was added onto the nylon membrane with MBTH. Then contact was made with the nylon membrane containing glutaraldehyde and MBTH and subsequently with the nylon membrane containing $FeCl_3$ to develop the blue color (Table 4). FIGS. 7A, 7B, 7C, 8A, 8B, and 8C show two different ways to develop the blue color. By separating the nylon containing MBTH and the nylon containing $FeCl_3$ with a liquid impermeable film or a blank nylon membrane, it allows the aldehyde to react with MBTH first. Any remaining MBTH then reacts with $FeCl_3$ to produce the blue color.

TABLE 4

Color Reaction of Glutaraldehyde on nylon containing MBTH and nylon containing $FeCl_3$

| Cidex Glutaraldehyde | Observation |
|---|---|
| Color blue | Color develops in less than 1 min and stabilizes for more than 10 minutes. |

Example 9

Device Design on Membrane, "Aldehyde Tester".

Figure 9:
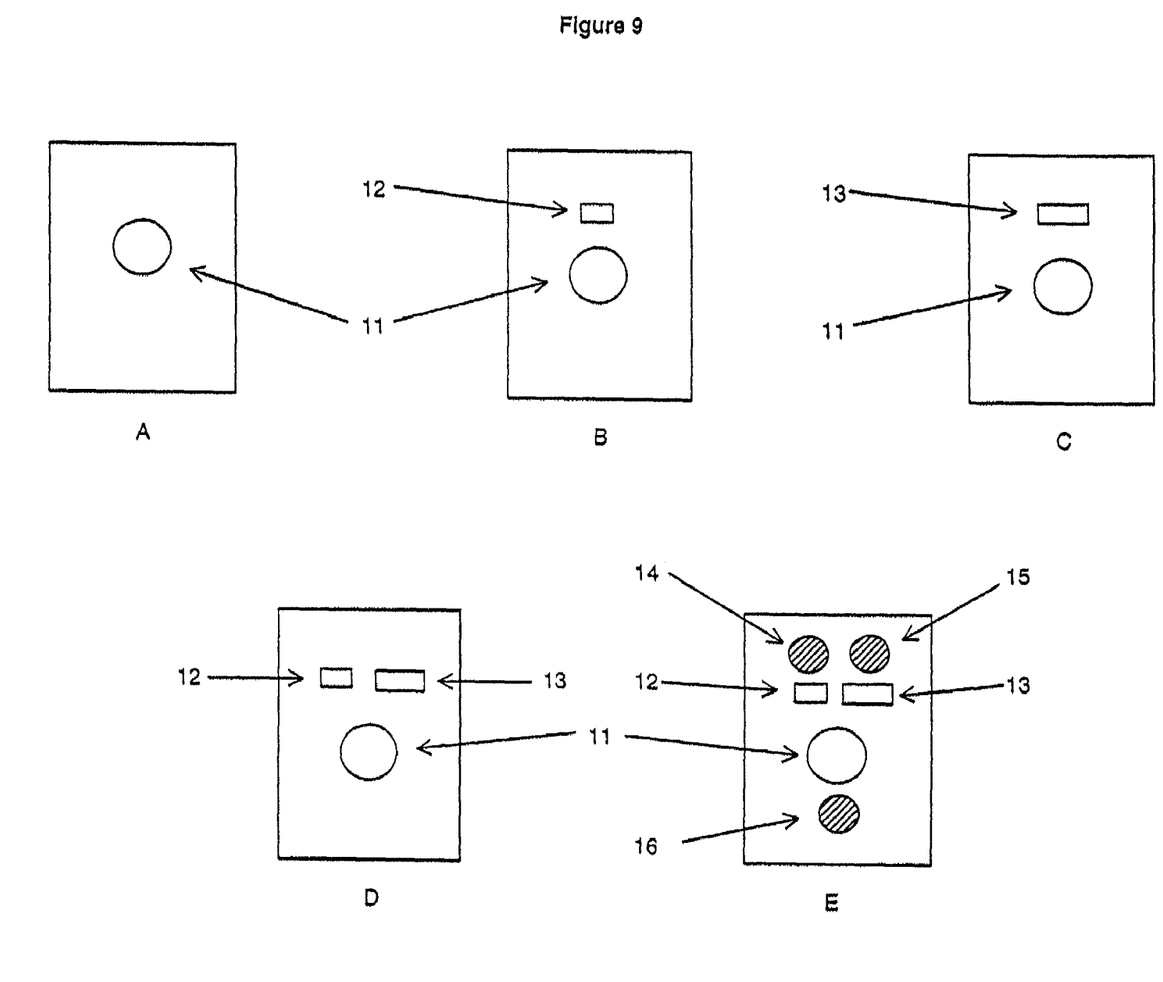
FIG. 9A shows a tester strip with an aldehyde indicator 11.
FIG. 9B shows a tester strip with an aldehyde indicator 11 and an aldehyde tester 12.
FIG. 9C shows a tester strip with an aldehyde indicator 11 and a pH tester 13.
FIG. 9D shows a tester strip with an aldehyde indicator 11, an aldehyde tester 12, and a pH tester 13.
FIG. 9E shows a tester strip with an aldehyde indicator 11, an aldehyde tester 12, a pH tester 13, and color comparators 14, 15, 16.

When MBTH is used as a limiting agent as described above, if the amount of aldehyde is around the point of interest then less aldehyde will produce more blue color. More accurately, this is only true if the aldehyde is still above a certain range. In the case of no aldehyde at all, for example, there will be no blue color formed since there is no azine formed (FIG. 1). Thus, to avoid confusion, an aldehyde tester 12 may be fabricated together on the membrane (FIG. 9B). Ideally this aldehyde tester could be separated from the main tester area 11 but close enough that diffusion of the aldehyde form the main tester area could reach the aldehyde tester region. This model will need only one single drop of the aldehyde solution. Schiff's reagent could be used for the test although other aldehyde reagents also could be used. Optionally, comparative color indicators may be integrated into the tester strip 14, 16.

Example 10

Device Design on Membrane, "pH Tester".

The pH of the Cidex glutaraldehyde solution is related to the efficacy of glutaraldehyde. In the hospital, the pH of the Cidex needs to be measured every time before use. Thus, a pH tester 13 could be fabricated into a device so that no separate pH measurement is necessary (FIGS. 9C–E). The principle is the same as for the "aldehyde tester." However, a properly chosen pH dye could be used. Single or mixture pH dyes could be used to effectively measure the pH range, usually in the pH 7–11 range. Examples include but are not limited to bromothymol blue, brilliant yellow, neutral red, rosolic acid, phenol red, 3-nitrophenol, orange II, phenolphthalein, o-cresolphthalein, nile blue A and thymolphthalein etc. A bar spectrum of different colors could be printed on the membrane chip or strip. The pH could be read directly by matching the color. In a preferred embodiment, the bar 15 should include pH 7–11.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of determining a concentration of an aldehyde in a test sample which is higher, equivalent or lower than a point of interest of the aldehyde wherein the point of interest is an effective concentration of the aldehyde comprising the steps of:
   (a) reacting the aldehyde in the test sample with an amount of MBTH to produce an azine, wherein said amount is the amount of MBTH that reacts with the aldehyde to the point of interest;
   (b) producing a first color if the concentration of said aldehyde is higher or equivalent to the point of interest; or
   (c) oxidizing any unreacted MBTH;
   (d) reacting the azine and any oxidized MBTH produced in step (c) to produce a second color different from the first color, the second color being indicative that the concentration of said aldehyde is lower than the point of interest;
   (e) observing an ending color in the test sample comprised of the first color and second colors; and
   (f) determining whether the effective concentration of aldehyde is present in the test sample based upon the ending color of in the test sample.

2. The method of claim 1, wherein the ending color in the test sample is blue, green, yellow or any combination thereof.

3. The method of claim 1, wherein the oxidant is selected from the group consisting of ferric chloride, potassium ferricyanide, lead tetraacetate and periodic acid.

4. The method of claim 1, wherein the oxidant is ferric chloride.

5. The method of claim 1, wherein the aldehyde is glutaraldehyde.

6. The method of claim 1, wherein the oxidant is mixed with the test sample at the same time as the MBTH reacts with the aldehyde.

7. The method of claim 1, wherein the oxidant is added to the test sample after the MBTH reacts with the aldehyde.

8. The method of claim 1 further comprising the step of drawing up a fixed volume of the aldehyde-containing test sample prior to performing step (a).

9. A method of determining a concentration of an aldehyde in a test sample which is higher, equivalent or lower than a point of interest of the aldehyde wherein the point of interest is an effective concentration of the aldehyde comprising the steps of:
   (a) drawing up a fixed volume of the aldehyde-containing test sample and loading the fixed volume to a measuring device having a gas or vapor permeable but liquid impermeable membrane;
   (b) reacting the aldehyde in the test sample with an amount of MBTH to produce an azine, wherein said amount is the amount of MBTH that reacts with the aldehyde to the point of interest;
   (c) producing a first color if the concentration of said aldehyde is higher or equivalent to the point of interest; or
   (e) oxidizing any unreacted MBTH;
   (f) reacting the azine and any oxidized MBTH produced in step (c) to produce a formazan producing a second color different from the first color, the second color being indicative that the concentration of said aldehyde is lower than the point of interest;
   (g) observing an ending color in the test sample comprised of the first color and second colors; and
   (h) determining whether the effective concentration of aldehyde is present in the test sample based upon the ending color of in the test sample.

10. The method of claim 1 further comprising the step of drawing up a fixed volume of the aldehyde-containing test sample and loading the fixed volume to a measuring device containing said MBTH.

11. The method of claim 8 further comprising applying the aldehyde in the test sample to an absorbent material.

12. A method of determining a concentration of an aldehyde in a test sample which is higher, equivalent or lower than a point of interest of the aldehyde wherein the point of interest is an effective concentration of the aldehyde comprising the steps of:
   (a) drawing up a fixed volume of the aldehyde-containing test sample and applying the aldehyde in the test sample to an absorbent material, wherein the absorbent material is a nylon membrane;
   (b) reacting the aldehyde in the test sample with an amount of MBTH to produce an azine, wherein said amount is the amount of MBTH that reacts with the aldehyde to the point of interest;

(c) producing a first color if the concentration of said aldehyde is higher or equivalent to the point of interest; or
(e) oxidizing any unreacted MBTH;
(f) reacting the azine and any oxidized MBTH produced in step (c) to produce a formazan producing a second color different from the first color, the second color being indicative that the concentration of said aldehyde is lower than the point of interest;
(g) observing an ending color in the test sample comprised of the first color and second colors; and
(h) determining whether the effective concentration of aldehyde is present in the test sample based upon the ending color of in the test sample.

13. The method of claim 11, wherein the absorbent material contains MBTH.

14. The method of claim 7, wherein substantially none of the second color is produced when the aldehyde equal to the point of interest.

15. The method of claim 6, wherein less of the second color is produced when the aldehyde is more than or the same as the point of interest than when the aldehyde is less than the point of interest.

16. The method of claim 1 wherein the reaction in step (d) produces a formazan to produce the second color.

17. The method of claim 8 further comprising loading the fixed volume to a measuring device containing said $FeCl_3$.

18. The method of claim 11, wherein the absorbent material contains said $FeCl_3$.

* * * * *